| United States Patent [19] | [11] Patent Number: 5,043,507 |
| Fukao et al. | [45] Date of Patent: Aug. 27, 1991 |

[54] PROCESS FOR PREPARING ALKYL-SUBSTITUTED AROMATIC HYDROCARBONS

[75] Inventors: Masami Fukao, Shiga; Takuo Hibi, Toyonaka; Kiyoshi Ikimi, Otokuni; Gohfu Suzukamo, Ibaraki, all of Japan

[73] Assignee: Sumitomo Chemical Company, Limited, Osaka, Japan

[21] Appl. No.: 399,974

[22] Filed: Aug. 29, 1989

[30] Foreign Application Priority Data

Aug. 31, 1988 [JP] Japan .................. 63-219502
Aug. 31, 1988 [JP] Japan .................. 63-219503
Sep. 2, 1988 [JP] Japan .................. 63-220845
Aug. 4, 1989 [JP] Japan .................. 1-203605

[51] Int. Cl.$^5$ .................. C07C 2/64; C07C 2/68; B01J 23/02
[52] U.S. Cl. .................. 585/452; 585/453; 585/467; 502/344
[58] Field of Search .................. 585/452, 453, 467; 502/344

[56] References Cited

U.S. PATENT DOCUMENTS

| 4,511,748 | 4/1985 | Kudoh et al. . | |
| 4,620,056 | 10/1986 | Shimizu et al. . | |
| 4,661,466 | 4/1987 | Drake et al. | 585/576 |
| 4,711,873 | 12/1987 | Suzukamo et al. . | |
| 4,727,213 | 2/1988 | Drake et al. | 585/576 |
| 4,822,764 | 4/1989 | Suzukamo et al. . | |

FOREIGN PATENT DOCUMENTS

| 0128001 | 12/1984 | European Pat. Off. . |
| 0173335 | 3/1986 | European Pat. Off. . |
| 1053229A | 8/1984 | Japan . |
| 1259535 | 8/1969 | United Kingdom . |
| 1269280 | 8/1969 | United Kingdom . |

OTHER PUBLICATIONS

"Carbanions Additions in the Reaction of Aromatic Hydrocarbons with Monoölefins", Herman Pines and Victor Mark, Mar. 14, 1956, pp. 4316–4322.

"Base-Catalyzed Reactions of Hydrocarbons and Related Compounds", Herman Pines and Wayne M. Stalick, Academic Press, 1977, pp. 240–380.

*Primary Examiner*—H. M. S. Sneed
*Assistant Examiner*—James Saba
*Attorney, Agent, or Firm*—Birch, Stewart, Kolasch & Birch

[57] ABSTRACT

An alkyl-substituted hydrocarbon is prepared by alkylating an alkyl aromatic hydrocarbon having at least one hydrogen atom at an alpha-position in a side chain with an olefin in the presence of a solid base which is obtainable by reacting an alumina with an alkali metal carbonate and/or aluminate and an alkali metal amd/or its hydride in an inert gas atmosphere at a temperature of 180° to 800° C. as a catalyst.

27 Claims, No Drawings

PROCESS FOR PREPARING ALKYL-SUBSTITUTED AROMATIC HYDROCARBONS

BACKGROUND OF THE INVENTION

1. Field of the Invention

The present invention relates to a process for preparing an alkyl-substituted aromatic hydrocarbon. More particularly, the present invention relates to a process for preparing an alkyl-substituted aromatic hydrocarbon by reacting an alkyl aromatic hydrocarbon having at least one hydrogen atom at an alpha-position in said alkyl side chain with an olefin in the presence of a solid base which is obtainable by reacting, in a specific temperature range, an alumina with at least one salt selected from the group consisting of carbonates and aluminates of alkali metals and at least one material selected from the group consisting of alkali metals and alkali metal hydrides, whereby the hydrogen atom at the alpha-position is substituted with an alkyl group.

2. Description of the Related Art

The alkyl-substituted aromatic hydrocarbons are useful as intermediates in the production of fine chemicals such as agricultural chemicals, pharmaceuticals and other chemicals and prepared by reacting the aromatic hydrocarbon having the hydrogen atom at the alpha-position in the side chain with the olefin in the presence of a base catalyst.

As the preparation process of the alkyl-substituted aromatic hydrocarbon, there are known a process which utilizes a catalyst comprising metal sodium and chlorotoluene and a process which utilizes a catalyst comprising metal sodium supported on potassium carbonate (cf. J. Am. Chem. Soc., 78, 4316 (1956), GB Patent No. 1269280 and Japanese Patent Kokai Publication No. 53229/1986).

However, the conventionally used catalysts have various drawbacks such as insufficient catalytic activities, a low yield of the alkyl-substituted hydrocarbon per a unit amount of the catalyst and troublesome separation of the catalysts from the product. Further, the conventional catalysts suffer from such problem that when they contact the moisture and/or oxygen in the air, they tend to lose their activities or they are ignited.

SUMMARY OF THE INVENTION

One object of the present invention is to provide a base catalyst which effectively catalyzes a reaction of an aromatic hydrocarbon having a hydrogen atom at the alphaposition in a side chain with an olefin and which can be easily separated from the product after reaction.

Another object of the present invention is to provide a process for producing an alkyl-substituted hydrocarbon by reacting the alkyl aromatic hydrocarbon having the hydrogen atom at the alpha-position in the side chain with the olefin.

Accordingly, the present invention provides a process for preparing an alkyl-substituted hydrocarbon comprising alkylating an alkyl aromatic hydrocarbon having at least one hydrogen atom at an alpha-position in a side chain with an olefin in the presence of a solid base which is obtainable by heating and reacting an alumina with at least one salt selected from the group consisting of carbonates and aluminates of alkali metals and at least one material selected from the group consisting of alkali metals and alkali metal hydrides at a temperature of from 180 to 800° C. in an inert gas atmosphere.

DETAILED DESCRIPTION OF THE INVENTION

The process of the present invention is characterized in the use of the specific solid base as the catalyst, which solid base is prepared by heating the alumina, the carbonate and/or aluminate of alkali metal and the alkali metal and/or its hydride at the specific temperature.

As the alumina, various types of aluminas except α-alumina are used. Preferred examples of the alumina are γ-alumina, χ-alumina, η-alumina and ρ-alumina. Among them, those having a relatively large surface area are preferred.

As the alkali metal or its hydride, an alkali metal of Group I of the Periodic Table such as lithium, sodium, potassium and rubidium or its hydride is used. They may be used as a mixture. Among them, sodium, potassium, sodium hydride, potassium hydride, or a mixture of them, particularly potassium and its hydride are preferred. The amount of the alkali metal or its hydride is generally from 2 to 15 % by weight based on the weight of the alumina.

Examples of the alkali metal carbonate and aluminate are lithium carbonate, sodium carbonate, potassium carbonate, rubidium carbonate, cesium carbonate, lithium hydrogen carbonate, sodium hydrogen carbonate, potassium hydrogen carbonate, rubidium hydrogen carbonate, cesium hydrogen carbonate, lithium aluminate, sodium aluminate, potassium aluminate, rubidium aluminate, cesium aluminate, etc. They may be used as a mixture. Among them, sodium carbonate, potassium carbonate, cesium carbonate, sodium aluminate and potassium aluminate are preferred. The amount of the alkali metal carbonate and/or aluminate is generally from 5 to 40 % by weight based on the weight of the alumina.

In the preparation of the solid base, preferably the alumina is reacted with the alkali metal carbonate and/or aluminate and then the resulting product is reacted with the alkali metal and/or its hydride, in the inert gas atmosphere.

As the inert gas, nitrogen, helium, argon and the like are used.

In the preparation of the solid base to be used in the process of the present invention, the reaction temperature is important. Usually, the reaction temperature is from 180 to 800° C. Preferably, when the alkali metal is used, the alumina and the alkali metal carbonate or aluminate are reacted in a temperature range of 180 to 600° C., more preferably in a temperature range of 250 to 480° C., and the alkali metal is reacted in a temperature range of 200 to 450° C. When the alkali metal hydride is used, the alumina and the alkali metal carbonate or aluminate are reacted in a temperature range of 200 to 700° C., more preferably 250 to 480° C., and the alkali metal hydride is reacted in a temperature range of 200 to 450° C.

The reaction time varies with other reaction conditions such as the reaction temperature. The reaction of the alumina with the alkali metal carbonate or aluminate may be completed within 0.5 to 10 hours, and the reaction with the alkali metal or its hydride may be completed within 10 to 300 minutes.

By the above reactions, the solid base which has high catalytic activity, good flowability and handleability can be obtained.

In the process of the present invention, the aromatic hydrocarbon having the hydrogen atom at the alphaposition in the side chain is reacted with the olefin in the presence of the above described solid base as the catalyst.

As such aromatic hydrocarbon, not only monocyclic aromatic hydrocarbons but also condensed polycyclic aromatic hydrocarbons may be used. In the aromatic hydrocarbons, the side chains may be closed to form a ring. Specific examples of the aromatic hydrocarbon are toluene, ethylbenzene, isopropylbenzene (cumene), n-propylbenzene, n-butylbenzene, sec.-butylbenzene, isobutylbenzene, xylene, cymene, diisopropylbenzene, methylnaphthalene, tetrahydronaphthalene, indan and the like Among them, toluene, ethylbenzene and isopropylbenzene are preferred.

As the olefin, those having 2 to 20 carbon atoms are usually used. The olefin may be straight or branched. The carbon-carbon double bond may be a terminal or internal double bond. Preferably, the olefin having the terminal double bond is used. Specific examples of the olefin are ethylene, propylene, 1-butene, 2-butene, isobutylene, 1-pentene, 2-pentene, 1-hexene, 2-hexene, 3-hexene, 1-heptene, 2-heptene, 3-heptene, octene, nonene, 3-methyl-1-butene, 2-methyl-2-butene, 3-methyl-1-pentene, the like. Among them, ethylene, propylene, 1-butene and 2-butene are preferred.

The alkylation reaction according to the present invention may be carried out batchwise or continuously with the use of a fluidized bed or a fix bed.

The reaction temperature for the alkylation is usually from 0 to 300° C., preferably from 10 to 200° C.

The reaction pressure is from atmospheric pressure to 200 kg/cm$^2$, preferably from 2 to 100 kg/cm$^2$.

The molar ratio of the olefin to the aromatic hydrocarbon is usually from 0.1 to 10, preferably from 0 2 to 5.

In the batchwise reaction, the amount of solid base catalyst to be used is from 0.01 to 20 % by weight, preferably from 0.05 to 5 % by weight based on the weight of the aromatic hydrocarbon. The reaction time is generally from 0.5 to 50 hours, preferably from 1 to 25 hours.

In the continuous reaction, the mixture of the aromatic hydrocarbon and the olefin in the above molar ratio is supplied at LHSV of 0.1 to 600 hr$^{-1}$, preferably 0.5 to 400 hr$^{-1}$.

According to the present invention, the alkylsubstituted hydrocarbon is effectively prepared in the presence of the solid base catalyst in a small amount under the mild conditions. Further, the catalyst to be used according to the present invention is easily handled and post-treated after the reaction.

PREFERRED EMBODIMENTS OF THE INVENTION

Practically and presently preferred embodiments of the present invention will be illustrated by following examples.

Preparation of Solid Bases

Solid Base A-1

An activated alumina of 42-200 mesh (NKHD-24, a trade name of Sumitomo Chemical Co., Ltd.) (26.5 g) was added to a solution of potassium carbonate (2.5 g) in water (50 g), and the aqueous mixture was evaporated at about 70° C. with a rotary evaporator.

The residue was stirred at 450° C for 3 hours in a nitrogen atmosphere and cooled to 290° C. Then, metal potassium (1.25 g) was added, and the mixture was stirred at the same temperature for 0.2 hour followed by cooling to room temperature to obtain Solid Base A-1 (24.7 g).

Solid Base A-2

In the same manner as in the preparation of Solid Base A-1 but using 2 g of metal potassium, Solid Base A-2 (25.5 g) was prepared.

Solid Base A-3

In the same manner as in the preparation of Solid Base A-1 but stirring the residue (before the addition of metal potassium) at 300° C and using 2 g of metal potassium, Solid Base A-3 was prepared.

Solid Base A-4

In the same manner as in the preparation of Solid Base A-1 but stirring the residue (before the addition of metal potassium) at 180° C. and using 2.38 g of metal potassium, Solid Base A-4 was prepared.

Solid Base A-5

In the same manner as in the preparation of Solid Base A-1 but stirring the residue (before the addition of metal potassium) at 700° C. and using 2 g of metal potassium, Solid Base A-5 was prepared.

Solid Base A-6

The same activated alumina as used in the preparation of Solid Base A-1 (26.5 g) and potassium carbonate (2.5 g) were ground and mixed, charged in a crucible and heated in a muffle furnace at 1,200° C. for 3 hours. After cooling to 200° C., the mixture was further cooled to room temperature in a desiccator in an atmosphere of nitrogen to obtain a fine powder.

The fine powder was heated to 290° C. in a nitrogen atmosphere. Then, to the heated powder, metal potassium (2.0 g) was added, and the mixture was stirred at the same temperature for 0.2 hour followed by cooling to room temperature to obtain Solid Base A-6.

Solid Base A-7

In the same manner as in the preparation of Solid Base A-1 but using sodium carbonate (2.5 g) in place of potassium carbonate and 2.41 g of metal potassium, Solid Base A-7 was prepared.

Solid Base A-8

In the same manner as in the preparation of Solid Base A-1 but using 2.17 g of metal sodium in place of metal potassium, Solid Base A-8 was prepared.

Solid Base A-9

In the same manner as in the preparation of Solid Base A-1 but using 42-200 mesh silica gel (#57 manufactured by Fuji-Davison Chemical Co., Ltd.), Solid Base A-9 was prepared.

Solid Base A-10

An activated alumina having a central particle size of 80 μm (BK-570, a trade name of Sumitomo Chemical Co., Ltd.) (50 g) was added to a solution of cesium carbonate (5.6 g) in water (100 g), and the aqueous mixture was evaporated at about 70° C. with a rotary evaporator.

The residue was stirred at 480° C. for one hour in a nitrogen atmosphere and cooled to 300° C. Then, metal potassium (2.84 g) was added, and the mixture was stirred at the same temperature for 0.5 hour followed by cooling to room temperature to obtain Solid Base A-10.

Solid Base A-11

After stirring potassium carbonate (50 g) at 350° C. for 2 hours in a nitrogen atmosphere and cooling it to 250° C., metal sodium (1.28 g) was added thereto, and the mixture was stirred at the same temperature for 5 hours followed by cooling to room temperature to obtain Solid Base A-11.

Solid Base A-12

The same activated alumina as used in the preparation of Solid Base A-1 (26.5 g) and potassium hydroxide (2.5 g) were ground and mixed, charged in a crucible and heated in a muffle furnace at 1,200° C. for 3 hours. After cooling to 200° C, the mixture was further cooled to room temperature in a desiccator in an atmosphere of nitrogen to obtain a fine powder.

The fine powder was heated to 290° C. Then, to the heated powder, metal sodium (2.0 g) was added, and the mixture was stirred at the same temperature for 0.5 hour followed by cooling to room temperature to obtain Solid Base A12.

Solid Base B-1

The same activated alumina as used in the preparation of Solid Base A-1 (26.5 g) was added to a solution of potassium aluminate (2.5 g) in water (50 g), and the aqueous mixture was evaporated at about 70° C. with a rotary evaporator.

The residue was stirred at 450° C. for 3 hours in a nitrogen atmosphere and cooled to 290° C. Then, metal potassium (2.0 g) was added, and the mixture was stirred at the same temperature for 0.2 hour followed by cooling to room temperature to obtain Solid Base B-1 (25.5 g).

Solid Base B-2

In the same manner as in the preparation of Solid Base B-1 but changing the temperature at which metal potassium was added and the mixture was stirred from 290° C. to 350° C., Solid Base B-2 was prepared.

Solid Base B-3

In the same manner as in the preparation of Solid Base B-1 but stirring the residue at 300° C., Solid Base B-3 was prepared.

Solid Base B-4

In the same manner as in the preparation of Solid Base B-1 but stirring the residue at 180° C. and using 2.35 g of potassium, Solid Base B-4 was prepared.

Solid Base B-5

In the same manner as in the preparation of Solid Base B-1 but stirring the residue at 700° C., Solid Base B-5 was prepared.

Solid Base B-6

The same activated alumina as used in the preparation of Solid Base A-1 (26.5 g) and potassium aluminate (2.5 g) were ground and mixed, charged in a crucible and heated in a muffle furnace at 1,200° C. for 3 hours. After cooling to 200° C., the mixture was further cooled to room temperature in a desiccator in an atmosphere of nitrogen to obtain a fine powder.

The fine powder was heated to 290° C. Then, to the heated powder, metal potassium (2.28 g) was added, and the mixture was stirred at the same temperature for 0.2 hour followed by cooling to room temperature to obtain Solid Base B-6.

Solid Base B-7

In the same manner as in the preparation of Solid Base B-6 but heating the mixture in the muffle furnace at 900° C. and using metal sodium (2.28 g) in place of metal potassium, Solid Base B-7 was prepared.

Solid Base B-8

In the same manner as in the preparation of Solid Base B-1 but using sodium aluminate (2.5 g) in place of potassium aluminate and 2.2 g of metal potassium, Solid Base B-8 was prepared.

Solid Base B-9

In the same manner as in the preparation of Solid Base B-1 but using metal sodium (2.3 g) in place of metal potassium, Solid Base B-9 was prepared.

Solid Base C-1

The same activated alumina as used in the preparation of Solid Base A-1 (26.5 g) was added to a solution of potassium carbonate (2.5 g) in water (50 g), and the aqueous mixture was evaporated at about 70° C. with a rotary evaporator.

The residue was stirred at 450° C. for 3 hours in a nitrogen atmosphere and cooled to 300° C. Then, potassium hydride (2.3 g) was added, and the mixture was stirred at the same temperature for 0.4 hour followed by cooling to room temperature to obtain Solid Base C-1 (25.9 g).

Solid Base C-2

In the same manner as in the preparation of Solid Base C-1 but stirring the residue at 250° C. and using 3.2 g of potassium hydride, Solid Base C-2 was prepared.

Solid Base C-3

In the same manner as in the preparation of Solid Base C-1 but stirring the residue at 300° C., Solid Base C-3 was prepared.

Solid Base C-4

In the same manner as in the preparation of Solid Base C-1 but stirring the residue at 700° C. and using 2.95 g of potassium hydride, Solid Base C-4 was prepared

Solid Base C-5

The same activated alumina as used in the preparation of Solid Base A-1 (26.5 g) and potassium carbonate (2.5 g) were ground and mixed, charged in a crucible and heated in a muffle furnace at 1,200° C. for 3 hours After cooling to 200° C., the mixture was further cooled to room temperature in a desiccator in an atmosphere of nitrogen to obtain a fine powder.

The fine powder was heated to 300° C. Then, to the heated powder, potassium hydride (2.88 g) was added, and the mixture was stirred at the same temperature for 0.4 hour followed by cooling to room temperature to obtain Solid Base C-5.

Solid Base C-6

In the same manner as in the preparation of Solid Base C-1 but using sodium carbonate (2.5 g) in place of potassium carbonate and 2.75 g of potassium hydride, Solid Base C-6 was prepared.

Solid Base C-7

In the same manner as in the preparation of Solid Base C-1 but using sodium hydride (2.7 g) in place of potassium hydride, Solid Base C-7 was prepared.

Solid Base D-1

The same activated alumina as used in the preparation of Solid Base A-1 (26.5 g) was added to a solution of potassium aluminate (2.5 g) in water (50 g), and the aqueous mixture was evaporated at about 70° C. with a rotary evaporator.

The residue was stirred at 450° C. for 3 hours in a nitrogen atmosphere and cooled to 300° C. Then, potassium hydride (2.3 g) was added, and the mixture was stirred at the same temperature for 0.4 hour followed by cooling to room temperature to obtain Solid Base D-1 (25.8 g).

Solid Base D-2

In the same manner as in the preparation of Solid Base D-1 but stirring the residue at 250° C. and using 2.85 g of potassium hydride, Solid Base D-2 was prepared.

Solid Base D-3

In the same manner as in the preparation of Solid Base D-1 but stirring the residue at 300° C., Solid Base D-3 was prepared.

Solid Base D-4

In the same manner as in the preparation of Solid Base D-1 but stirring the residue at 700° C., Solid Base D-4 was prepared.

Solid Base D-5

In the same manner as in the preparation of Solid Base D-1 but using sodium aluminate (2.5 g) in place of potassium aluminate and 2.4 g of potassium hydride, Solid Base D-5 was prepared.

D-6

In the same manner as in the preparation of Solid Base D-1 but using sodium hydride (2.7 g) in place of potassium hydride, Solid Base D-6 was prepared.

Solid Base D-7

The same activated alumina as used in the preparation of Solid Base A-1 (26.5 g) and potassium aluminate were ground and mixed, charged in a crucible and heated in a muffle furnace at 1,200° C. for 3 hours. After cooling to 200° C., the mixture was further cooled to room temperature in a desiccator in an atmosphere of nitrogen to obtain a fine powder.

The fine powder was heated to 300° C. Then, to the heated powder, potassium hydride (2.43 g) was added, and the mixture was stirred at the same temperature for 0.4 hour followed by cooling to room temperature to obtain Solid Base D-7.

EXAMPLE 1

In a 600 ml autoclave equipped with a magnetic stirrer, Solid Base A-1 (0.63 g) and cumene (240 g) were charged under nitrogen, heated to 40° C while stirring at 1,000 rpm and then reacted at the same temperature for 3 hours while supplying ethylene gas under pressure of 10 kg/cm$^2$G. to produce tert.-amylbenzene (hereinafter referred to as "TAB").

After the reaction, the autoclave was cooled, and the catalyst was filtered off. The reaction mixture was analyzed with gas chromatography. The results are shown in Table 1.

The selectivity of TAB is calculated according to the following equation:

$$\text{Selectivity (\%)} = \frac{\text{Amount of produced TAB (mole)} \times 100}{\text{Total amount of all produced alkyl-substituted compounds (mole)}}$$

EXAMPLES 2–32 AND COMPARATIVE EXAMPLES 1–3 AND 5–7

In the same manner as in Example 1 but using each of Solid Bases A-2 to A-9, A-12, B-1 to B-9, C-1 to C-7 and D-1 to D-7, supplying the ethylene gas under pressure of 2 kg/cm$^2$G in Example 3, using 160 g of cumene in Comparative Example 3 and carrying out the reaction under the conditions shown in Table 1, the alkylation was carried out. The results are shown in Table 1.

In Examples 1 through 32, the catalysts were still active at the end of the reaction and the alkylation could be further carried out by using the same catalysts.

TABLE 1

| Example No. | Solid Base | (g) | Reaction Temp. (°C.) | Reaction time (hrs) | Conversion of cumene (%) | Selectivity of TAB (%) |
|---|---|---|---|---|---|---|
| 1 | A-1 | (0.63) | 40 | 3 | 98.0 | 99.3 |
| 2 | ↑ | (1.26) | 25 | 3.5 | 99.9 | 99.2 |
| 3 | ↑ | (0.58) | 160 | 3 | 81.3 | 99.1 |
| 4 | ↑ | (0.38) | ↑ | 1.5 | 93.4 | 99.7 |
| 5 | A-7 | (0.39) | ↑ | ↑ | 44.4 | 96.2 |
| 6 | A-8 | (0.44) | ↑ | ↑ | 56.0 | 99.4 |
| 7 | A-4 | (0.40) | ↑ | ↑ | 63.7 | 98.9 |
| 8 | A-3 | (0.43) | ↑ | ↑ | 76.5 | 99.0 |
| 9 | A-2 | (0.39) | ↑ | ↑ | 93.3 | 99.7 |
| 10 | A-5 | (1.20) | ↑ | ↑ | 31.7 | 87.2 |
| C. 1 | A-6 | (1.32) | ↑ | ↑ | 18.4 | 69.4 |
| C. 2 | A-9 | (1.95) | ↑ | 3 | 0.13 | 83.2 |
| C. 3 | A-12 | (0.98) | ↑ | 1.5 | 7.5 | 98.4 |
| C. 4 | Mixture (8.49) | | ↑ | 3 | 19.4 | 73.9 |
| 11 | B-1 | (0.44) | 100 | 1.5 | 99.8 | 98.2 |
| 12 | B-2 | (0.38) | 160 | ↑ | 68.5 | 99.0 |
| 13 | B-8 | (0.40) | ↑ | ↑ | 65.0 | 96.8 |
| 14 | B-9 | (0.50) | ↑ | ↑ | 22.7 | 98.1 |
| 15 | B-4 | (1.17) | ↑ | ↑ | 47.0 | 99.7 |
| 16 | B-3 | (0.63) | ↑ | ↑ | 70.5 | 99.0 |
| 17 | B-1 | (0.47) | ↑ | ↑ | 92.4 | 98.2 |
| 18 | B-5 | (0.36) | ↑ | ↑ | 22.0 | 85.2 |
| C. 5 | B-6 | (0.90) | ↑ | ↑ | 17.5 | 68.9 |
| C. 6 | B-7 | (1.53) | ↑ | ↑ | 33.1 | 95.5 |
| C. 3 | A-12 | (0.98) | ↑ | ↑ | 7.5 | 98.4 |
| C. 4 | Mixture (8.49) | | ↑ | 3 | 19.4 | 73.9 |
| 19 | C-1 | (0.42) | 100 | 1.5 | 99.8 | 98.7 |
| 20 | C-6 | (0.39) | 160 | ↑ | 67.8 | 98.9 |
| 21 | C-7 | (0.43) | ↑ | ↑ | 64.5 | 99.4 |
| 22 | C-2 | (0.48) | ↑ | ↑ | 95.6 | 99.7 |
| 23 | C-3 | (0.44) | ↑ | ↑ | 99.8 | 99.3 |
| 24 | C-1 | (0.44) | ↑ | ↑ | 81.3 | 99.6 |
| 24 | C-4 | (0.41) | ↑ | ↑ | 59.0 | 93.7 |
| C. 3 | A-12 | (0.98) | ↑ | ↑ | 7.5 | 98.4 |
| C. 4 | Mixture | | ↑ | 3 | 19.4 | 73.9 |

TABLE 1-continued

| Example No. | Solid Base (g) | | Reaction Temp. (°C.) | Reaction time (hrs) | Conversion of cumene (%) | Selectivity of TAB (%) |
| --- | --- | --- | --- | --- | --- | --- |
| | | (8.49) | | | | |
| 26 | D-1 | (0.44) | 100 | 1.5 | 98.7 | 97.8 |
| 27 | D-5 | (0.43) | 160 | ↑ | 96.4 | 99.3 |
| 28 | D-6 | (0.45) | ↑ | ↑ | 23.1 | 99.0 |
| 29 | D-2 | (0.43) | ↑ | ↑ | 99.4 | 99.7 |
| 30 | D-3 | (0.39) | ↑ | ↑ | 99.9 | 99.6 |
| 31 | D-1 | (0.45) | ↑ | ↑ | 88.9 | 97.3 |
| 32 | D-4 | (0.44) | ↑ | ↑ | 56.7 | 92.7 |
| C. 7 | D-7 | (1.29) | ↑ | ↑ | 24.3 | 91.8 |
| C. 3 | A-12 | (0.98) | ↑ | ↑ | 7.5 | 98.4 |
| C. 4 | Mixture (8.49) | | ↑ | 3 | 19.4 | 73.9 |

COMPARATIVE EXAMPLE 4

To a 200 ml autoclave equipped with a magnetic stirrer, anhydrous potassium carbonate which had been calcined at 400° C. for 2 hours in a nitrogen atmosphere (8.19 g), metal sodium (0.30 g) and cumene (26.7 g) were charged under nitrogen, heated to 190° C. while stirring at 1,000 rpm then stirred at the same temperature for 2 hours.

After cooling the autoclave to 25° C., additional cumene (53.3 g) was added and the mixture was heated to 160° C. while stirring at 1,000 rpm and then reacted at the same temperature for 3 hours while supplying ethylene gas under pressure of 10 kg/cm²G.

After the reaction, the product was analyzed in the same manner as in Example 1. The conversion of cumene was 19.4 % and the selectivity of TAB was 73.9 %.

EXAMPLE 33

In a 300 ml autoclave equipped with a magnetic stirrer, Solid Base A-1 (0.84 g) and cumene (80 g) were charged under nitrogen and then liquid propylene (90 ml) was injected under pressure. The reaction was then carried out at 160° C. for 24 hours while stirring to produce 1,1,2-trimethylpropylbenzene (hereinafter referred to as "TMPB").

After the reaction, the autoclave was cooled, and the reaction mixture was analyzed in the same manner as in Example 1. The results are shown in Table 2.

The selectivity of TMPB is calculated according to the following equation:

$$\text{Selectivity (\%)} = \frac{\text{Amount of produced } TMPB \text{ (mole)} \times 100}{\text{Total amount of all produced alkyl-substituted compounds (mole)}}$$

EXAMPLES 34–37 AND COMPARATIVE EXAMPLE 8

In the same manner as in Example 33 but using Solid Base A-10, B-1, C-1, D-1 or A-11 in place of Solid Base A-1, the alkylation was carried out.

After the reaction, the autoclave was cooled, and the reaction mixture was analyzed in the same manner as in Example 1. The results are shown in Table 2.

In Examples 33 through 37, the catalysts were still active at the end of the reaction and the alkylation could be further carried out by using the same catalysts.

COMPARATIVE EXAMPLE 9

In a 300 ml autoclave equipped with a magnetic stirrer, anhydrous potassium carbonate which had been calcined at 400° C. for 2 hours in a nitrogen atmosphere (8.86 g), metal sodium (0.30 g) and cumene (81.2 g) were charged under nitrogen, heated to 190° C. while stirring at 1,000 rpm and then stirred at the same temperature for 2 hours.

After cooling the autoclave, liquid propylene (70 ml) was injected under pressure and the mixture was stirred at 160° C. at 1,000 rpm for 24 hours.

After the reaction, the produce was analyzed in the same manner as in Example 1. The results are shown in Table 2.

TABLE 2

| Example No. | Solid Base (g) | | Propylene (ml) | Conversion of cumene (%) | Selectivity of TMPB (%) |
| --- | --- | --- | --- | --- | --- |
| 33 | A-1 | (0.84) | 90 | 82.9 | 86.4 |
| 34 | A-10 | (1.31) | 93 | 92.8 | 85.8 |
| 35 | B-1 | (0.96) | 100 | 63.1 | 87.0 |
| 36 | C-1 | (0.84) | 100 | 66.9 | 84.2 |
| 37 | D-1 | (0.70) | 100 | 45.9 | 87.4 |
| C. 8 | A-11 | (1.37) | 80 | 13.1 | 82.0 |
| C. 9 | Mixture (9.16) | | 70 | 8.0 | 81.5 |

EXAMPLE 19

In a 300 ml autoclave equipped with a magnetic stirrer, Solid Base A-01 (2.53 g) and toluene (79.4g) were charged under nitrogen and then liquid propylene (70 ml) was injected under pressure. The reaction was carried out at 164° C. for 6 hours while stirring at 1,000 rpm to produce isobutylbenzene (hereinafter referred to as "IBB").

After the reaction, the product was analyzed in the same manner as in Example 1. The results are shown in Table 3.

The selectivity of IBB is calculated according to the following equation:

$$\text{Selectivity (\%)} = \frac{\text{Amount of produced } IBB \text{ (mole)} \times 100}{\text{Total amount of all produced alkyl-substituted compounds (mole)}}$$

EXAMPLES 39–42 AND COMPARATIVE EXAMPLE 10

In the same manner as in Example 38 but using Solid Base A-2, B-1, C-1, D-1 or A-6 in place of Solid Base A-1, the alkylation was carried out.

After the reaction, the product was analyzed in the same manner as in Example 1. The results are shown in Table 3.

In Examples 39–42, the catalysts were still active at the end of the reaction and the alkylation could be further carried out by using the same catalysts.

COMPARATIVE EXAMPLE 11

In a 200 ml autoclave equipped with a magnetic stirrer, anhydrous potassium carbonate which had been calcined at 400° C. for 2 hours in a nitrogen atmosphere (8.45 g), metal sodium (0.3 g) and toluene (26.6 g) were charged under nitrogen, heated to 190° C. while stirring at 1,000 rpm and then stirred at the same temperature for 2 hours.

After cooling the autoclave, additional toluene (53.2 g) was added and liquid propylene (70 ml) was injected under pressure. Then the mixture was stirred at 160° C. for 6 hours.

After the reaction, the product was analyzed in the same manner as in Example 1. The results are shown in Table 3.

TABLE 3

| Example No. | Solid Base (g) | | Conversion of toluene (%) | Selectivity of IBB (%) |
|---|---|---|---|---|
| 38 | A-1 | (2.53) | 32.0 | 91.1 |
| 39 | A-2 | (4.42) | 44.6 | 92.6 |
| 40 | B-1 | (3.56) | 30.7 | 92.0 |
| 41 | C-1 | (2.54) | 24.0 | 91.9 |
| 42 | D-1 | (2.77) | 26.0 | 93.0 |
| C. 10 | A-6 | (4.57) | 13.5 | 90.7 |
| C. 11 | Mixture (8.75) | | 3.5 | 89.2 |

What is claimed is:

1. A process for preparing an alkyl-substituted hydrocarbon comprising alkylating an alkyl aromatic hydrocarbon having at least one hydrogen atom at an alphaposition in a side chain with an olefin int he presence of a solid base which is obtainable by heating and reacting an alumina with at least one aluminate of an alkali metal and at least one material selected from the group consisting of alkali metals and alkali metal hydrides at a temperature of from 180 to 800° C. in an inert gas atmosphere.

2. The process according to claim 1, wherein the alkali metal or its hydride is reacted at a temperature of 200 to 450° C.

3. The process according to claim 1, wherein the aluminate is reacted at a temperature of 180 to 600° C., and then the alkali metal is reacted at a temperature of 200 to 450° C.

4. The process according to claim 1, wherein the aluminate is reacted at a temperature of 200 to 700° C., and then the alkali metal is reacted at a temperature of 200 to 450° C.

5. The process according to claim 1, wherein the aluminate is reacted at a temperature of 250 to 480° C.

6. The process according to claim 1, wherein the amount of the aluminate is from 5 to 40% by weight based on the weight of the alumina.

7. The process according to claim 1, wherein the amount of alkali metal or its hydride is from 2 to 15% by weight based on the weight of the alumina.

8. The process according to claim 1, wherein the solid base is one prepared by reacting the alumina with the alkali metal aluminate and then with the alkali metal.

9. The process according to claim 1, wherein the solid base is one prepared by reacting the alumina with the alkali metal aluminate and then with the alkali metal hydride.

10. The process according to claim 1, wherein the alkali metal aluminate is at least one selected from the group consisting of sodium aluminate and potassium aluminate.

11. The process according to claim 1, wherein the alkali metal is at least one selected form the group consisting of sodium, potassium and a mixture thereof.

12. The process according to claim 1, wherein the alkali metal hydride is at least one selected from the group consisting of sodium hydride, potassium hydride and a mixture thereof.

13. The process according to claim 1, wherein the aromatic hydrocarbon having the hydrogen atom at the alphaposition in the side chain has 1 to 10 carbon atoms in the side chain.

14. The process according to claim 13, wherein the aromatic hydrocarbon is at least one selected from the group consisting of toluene, isopropylbenzene and diisopropylbenzene.

15. The process according to claim 1, wherein the olefin has 2 to 20 carbon atoms.

16. The process according to claim 15, wherein the olefin is selected from the group consisting of ethylene and propylene.

17. The process according to claim 1, wherein the alkylation temperature is from 20 to 200° C.

18. The process according to claim 1, wherein the alumina is a member selected form the group consisting of $\gamma$-alumina, $\chi$-alumina, $\eta$-alumina and $\rho$-alumina.

19. The process according to claim 1, wherein the alkali metal and alkali metal hydride is at least one selected from the group consisting of potassium, potassium hydride and a mixture thereof 20. The process according to claim 1, wherein the molar ratio of the olefin to the aromatic hydrocarbon is from 0.1 to 10.

21. The process according to claim 1, wherein the molar ratio of the olefin to the aromatic hydrocarbon is from 0.2 to 5.

22. The process according to claim 1, wherein the amount of the solid base is from 0.01 to 20% by weight based on the weight of the alkyl aromatic hydrocarbon.

23. The process according to claim 21, wherein the amount of the solid base is from 0.5 to 5% by weight based on the weight of the alkyl aromatic hydrocarbon.

24. The process according to claim 1, wherein the reaction time is from 1 to 25 hours.

25. The process according to claim 1, wherein the process is continuous and a mixture of the alkyl aromatic hydrocarbon and the olefin is supplied to the solid base at LHSV of the 0.5 to 400 hr$^{-1}$.

26. The process according to claim 1, wherein the alkyl aromatic hydrocarbon is at least one selected from the group consisting of toluene, ethylbenzene, isopropylbenzene, n-propylbenzene, xylene, cymene, diisopropylbenzene, methylnaphthalene, tetrahydronaphthalene, and indan.

27. The process according to claim 1, wherein the olefin is at least one member selected form the group consisting of ethylene, propylene, 1-butene, 2-butene, isobutylene, 1-pentene, 2-pentene, 1-hexene, 2-hexene, 3-hexene, 1-heptene, 2-heptene, 3-heptene, octene, nonene, 3-methyl-1-butene, 2-methyl-2-butene, 3-methyl-1-pentene, and 3-methyl-2-pentene.

* * * * *